United States Patent [19]
Mombaerts et al.

[11] Patent Number: 5,859,307
[45] Date of Patent: Jan. 12, 1999

[54] MUTANT RAG-1 DEFICIENT ANIMALS HAVING NO MATURE B AND T LYMPHOCYTES

[75] Inventors: Peter Mombaerts, Cambridge; Susumu Tonegawa, Newton; Randall S. Johnson, Boston; Virginia Papaioannou, Lexington, all of Mass.

[73] Assignees: Massachusetts Institute of Technology, Cambridge; Dana Farber Cancer Institute & Tufts University, Boston, both of Mass.

[21] Appl. No.: 254,989

[22] Filed: Jun. 7, 1994

Related U.S. Application Data

[63] Continuation of Ser. No. 830,831, Feb. 4, 1992, abandoned.
[51] Int. Cl.$^6$ .......................... A61K 49/00; G01N 31/00; C12N 5/06; C12N 15/06
[52] U.S. Cl. ................................ 800/2; 424/9.1; 424/9.2; 435/172.3; 435/240.2; 435/240.21
[58] Field of Search ...................... 536/23.1; 435/172.3, 435/317.1, 240.2, 320.1, 240.21; 800/2, DIG. 1; 935/111; 424/9.1, 9.2

[56] References Cited

U.S. PATENT DOCUMENTS 4,736,866  4/1988  Leder et al. ................................ 800/2

OTHER PUBLICATIONS

Koller et al., Science 248:1227–1230 (1990).
Zimmer et al., Nature 338:150–153 (1989).
Robertson, Biology of Reprod. 44:238–245 (1991).
Mosien, J. Clinical Immunol. 10(4):185–191 (1990).
Mansour, GATA 7(8):219–227 (1990).
Adra, C.N., et al., "Cloning and expression of the mouse pgk–1 gene and the nucleotide sequence of its promoter," 60 *Gene* 65–74 (1987).
Alt F.W. et al., "DNA recombination in the brain?" 1 *Curr. Biol.* 3–5 (1991).
Alt, F.W., et al., "Regulation of Genome Rearrangement Events during Lymphocyte Differentiation," 89 *Immunol. Rev.* 5–30 (1986).
Alt, F., et al., "Organization and Reorganization of Immunoglobulin Genes in A–MuLV–Transformed Cells: Rearrangement of Heavy but Not Light Chain Genes," 27 *Cell* 381–390 (Dec. 1981).
Alt., F.W., et al., "Ordered rearrangement of immunoglobulin heavy chain variable region segments," 3(6) *EMBO J.* 1209–1219 (1984).
Boehm, T., et al., "A simple technique for generating probes for RNA in situ hybridization: An adjunct to genome mapping exemplified by the RAG–1/RAG–2 gene cluster," 88 *Proc. Natl. Acad. Sci. USA* 3927–3931 (May 1991).
Bosma, G.C., et al., "Evidence of Functional Lymphocytes in Some (Leaky) Scid Mice," 167 *J. Exp. Med.* 1016–1033 (Mar. 1988).

Bosma, G.C., et al., "A severe combined immunodeficiency mutation in the mouse," 301 *Nature* 527–530 (Feb. 10, 1983).
Bosma, M.J., & A.M. Carroll. "The Scid Mouse Mutant: Definition, Characterization, and Potential Uses," 9 *Ann. Rev. Immunol.* 323–350 (1991).
Bradley, A., "Production and analysis of chimaecric mice," 113–151 (19 ).
Capecchi, M.R., "Altering the Genome by Homologous Recombination," 244 *Science* 1288–1292 (Jun. 11, 1989).
Carlson, L.M., et al., "Selective Expression of RAG–2 in Chicken B Cells Undergoing Immunoglobulin Gene Conversion," 64 *Cell* 201–208 (Jan. 11, 1991).
Carroll, A.M., et al., "Occurrence of Mature B (IGM$^+$, B220$^+$) and (CD3$^+$) Lymphocytes in Scid Mice," 143 *J. Immunol*, 1087–1093 (1989).
Carroll, A.M., & M.J. Bosma, "Detection and characterization of functional T cells in mice with severe combined immune deficiency," 18 *Eur. J. Immunol.* 1965–1971 (1988).
Carroll, A.M., & M.J. Bosma, "T–lymphocyte development in scid mice is arrested shortly after the initiation of T–cell receptor δ gene recombination," 5 *Genes Dev.* 1357–1366 (1991).
Chien, Y., et al., "T–cell receptor δ gene rearrangements in early thymocytes," 330 *Nature* 722–727 (Dec. 1987).
Chun. J.J.M., et al., "The Recombination Activating Gene–1 (RAG–1) Transcript Is Present in the Murine Central Nervous System," 64 *Cell* 189–200 (Jan. 11, 1991).
Davis, M.M., and P.J. Bjorkman, "T–cell antigen receptor genes and T–cell recognition," 334 *Nature* 395–402 (Aug. 4, 1988).
Davis, M.M., "Molecular Genetics of the T Cell–Receptor Beta Chain," 3 *Ann. Rev. Immunol.* 537–560 (1985).
Early, P., et al., "An Immunoglobin Heavy Chain Variable Region Is Generated from Three Segments of DNA: $V_H$, D and $J_H$," 19 *Cell* 981–992 (Apr. 1980).

(List continued on next page.)

*Primary Examiner*—Brian R. Stanton
*Attorney, Agent, or Firm*—Arnall Golden & Gregory LLP

[57] ABSTRACT

Immunodeficient animals are generated by introducing a mutation in RAG-1 into the germline of the animals via gene targeting in embryonic stem cells. The production of mutant RAG-1 deficient mice is detailed. RAG-1 deficient mice have no mature B and T lymphocytes. The arrest of B and T cell differentiation occurs at an early stage and correlates with the inability to perform V(D)J recombination. To date, these mice do not have mature B and T lymphocytes, nor do they express immunoglobulin or T cell receptors. The same strategy can be applied to the generation of other RAG-1 deficient animals, such as rabbits, rats, and pigs, using known techniques. These animals are all useful for the same general purposes as the scid mice, for example, cultivation of human lymphocytes for expression of human immunoglobulin. Other uses include the establishment of continuous lymphoid cell lines and, by crossbreeding with other lines of animals, the establishment of animals developing tumors for use in studying tumor cell developments and treatments.

13 Claims, 1 Drawing Sheet

OTHER PUBLICATIONS

Evans, M.J., & M.H. Kaufman, "Establishment in culture of pluripotential cells from mouse embryos," 292 *Nature* 154–156 (Jul. 9, 1981).

Fulop, G.M., et al., "Early B–Cell Precursors in scid Mice: Normal Numbers of Cells Transformable with Abelson Murine Leukemia Virus (A–MuLV)," 113 *Cell. Immunol.* 192–201 (1988).

Fulop, G.M., & R.A. Phillips, "The scid mutation in mice causes a general defect in DNA repair," 347 *Nature* 479–482 (Oct. 4, 1990).

Gossler, A., et al., "Transgenesis by means of blastocyst–derived embryonic stem cell lines," 83 *Proc. Natl. Acad. Sci. USA* 9065–9069 (Dec. 1986).

Hendrickson, E.A., et al., "A link between double–strand break–related repair and V(D)J recombination: The scid mutation," 88 *Proc. Natl. Acad. Sci. USA* 4061–4065 (May 1991).

Hesse, J.E., et al., "V(D)J recombination: a functional definition of the joining signals," 3 *Genes Dev.* 1053–1061 (1989).

Joyner, A.L., et al., "Subtle Cerebellar Phenotype in Mice Homozygous for a Targeted Deletion of the En–2 Homeobox," 251 *Science* 1239–1243 (Mar. 8, 1991).

Laird, P.W., et al., "Simplified mammalian DNA isolation procedure," 19(15) *Nucleic Acids Research* 4293 (1991).

Malissen, M., et al., "Mouse T Cell Antigen Receptor: Structure and Organization of Constant and Joining Gene Segments Encoding the β Polypeptide," 37 *Cell* 1101–1110 (1984).

Mansour, S.L., et al., "Disruption of the proto–oncogene int–2 in mouse embryo–derived stem cells:; a general strategy for targeting mutations to non–selectable genes," 336 *Nature* 348–352 (Nov. 24, 1988).

Max, E.E., et al., "Sequences of five potential recombination sites encoded close to an immunogloblin K constant region gene," 76(7) *Proc. Natl. Acad. Sci. USA* 3450–3454 (Jul. 1979).

McCune, J.M., "SCID mice as immune system models," 3 *Curr. Op. Immunol.* 224–228 (1991).

MaMahon, A.P. & A. Bradley, "The Wnt–1 (int–1) Proto–Oncogene Is Required for Development of a Large Region of the Mouse Brain," 62 *Cell* 1073–1085 (Sep. 21, 1990).

Mombaerts, P., et al., "Creation of a large genomic deletion at the T–cell antigen receptor β–subunit locus in mouse embryonic stem cells by gene targeting", 88 *Proc. Natl. Acad. USA* 3084–3087 (Apr. 1991).

Nowakowski, R.S., "The Mode of Inheritance of a Defect in Lamination in the Hippocampus of BALB/c Mice," 1 *J. Neurogen.* 249–258 (1984).

Oettinger, M.A., et al., "RAG–1 and RAG–2, Adacent Genes That Synergistically Activate V(D)J Recombination," 248 *Science* 1517–1523 (Jun. 22, 1990).

Perry, R.P., et al., "Organization and expression of immunoglobulin genes in fetal liver hybridomas," 78 *Proc. Natl. Acad. Sci. USA* 247–251 (Jan. 1981).

Raulet, D.H., et al., "Developmental regulation of T–cell receptor gene expression," 314 *Nature* 103–107 (Mar. 1985).

Reth, M.G., et al., "Regulated progression of a cultured pre–B–cell stage," 317 *Nature* 353–355 (Sep. 26, 1985).

Robertson, E.J., "Embryo–derived stem cell lines" in Teratocarcinomas and embryonic stem cells: A practical approach, E.J. Robertson, ed., 71–112, IRL Press, (1987).

Rosenberg, N., & D. Baltimore, "A Quantitative Assay for Transformation of Bone Marrow Cells by Abelson Murine Leukemia Virus," 143 *J. Exp. Med.* 1453–1463 (1976).

Sakaguchi, N. & F. Melchers, "λ 5, a new light–chain–related locus selectively expressed in pre–B lymphocytes," 324 *Nature* 579–582 (Dec. 11, 1986).

Sakano, H., et al., "Sequences at the somatic recombination sites of immunoglobulin light–chain genes," 280 *Nature* 288–294 (Jul. 1979).

Sakano, H., et al., "Identification and nucleotide sequence of a diversity DNA seqment (D) of immunoglobulin heavy–chain genes," *Nature* 562–565 (Apr. 16, 1981).

Sakano, H., et al., "Two types of somatic recombination are necessary for the generation of complete immunoglobulin heavy–chain genes," 286 *Nature* 676–683 (Aug. 14, 1980).

Samelson, L.E., et al., "Expression of genes of the T–cell antigen receptor complex in precursor thymycytes," 315 *Nature* 765–768 (Jun. 27, 1985).

Schatz, D.G., et al., "The V(D)J Recombination Activating Gene, RAG–1," 59 *Cell* 1035–1048 (Dec. 22, 1989).

Schatz, D.G., & D. Baltimore, "Stable Expression on Iimmunoglobulin Gene V(D)J Recombinase Activity by Gene Trasfer into 3T3 Fibroblasts," 53 *Cell* 107–115 (Apr. 8, 1988).

Shinkai, Y., et al., "RAG–2–deficient mice lack mature lymphocytes owing to inability in initiate V)D)J rearrangement," 68(5) *Cell* 68(5) *Cell* 855–867 (Mar. 6, 1992).

Snodgrass, H.R., et al., "Expression of T–cell antigen receptor genes during fetal development in the thymus," 315 *Nature* 232–233 (May 16, 1985).

Tonegawa, S., "Somatic generation of antibody diversity," 302 *Nature* 575–581 (Apr. 14, 1983).

Turka, L.A., et al., "Thymocyte Expression of RAG–1 and RAG–2: Termination by T Cell Receptor Cross–Linking," 253 *Science* 778–781 (Aug. 16, 1991).

Tybulewicz, V.L.J., et al., "Neonatal Lethality and Lymphopenia in Mice with a Homozygous Disruption of the c–abl Proto–Oncogene," 65 *Cell* 1153–1163 (Jun. 28, 1991).

von Boehmer, H., "The Developmental Biology of T–lymphocytes," 6 *Ann. Rev. Immunol.* 309–326 (1988).

Yancopoulos, G.D., et al., "Introduced T Cell Receptor Variable Region Gene Seqments Recombine in Pre–B Cells: Evidence That B and T Cells Use a Common Recombinase," 44 *Cell* 251–259 (Jan. 3, 1986).

Maki, R., et al. "Immunoglobulin Gene Rearrangement in Immature B Cells" 209 *Science* 1366–1369 (Sep. 19, 1980).

MUTANT RAG-1 DEFICIENT ANIMALS HAVING NO MATURE B AND T LYMPHOCYTES

This is a continuation of application Ser. No. 07/830,831 filed on Feb. 4, 1992 now abandoned.

The United States government has rights in this invention by virtue of grants from the National Institutes of Health, grant numbers 5R35-CA53874-02 (ST) and HD27295 (VEP).

BACKGROUND OF THE INVENTION

This invention is generally in the area of immunodeficient mutant animals and methods of use thereof.

Assembly of immunoglobulin (Ig) heavy and light chain genes and of $\alpha$ and $\beta$ chain genes of the T cell receptor (TCR) is mediated to a large extent in developing lymphocytes by somatic recombination, in which widely separated gene segments are joined to form a complete variable region, a process known as V(D)J recombination, described by Tonegawa, S. *Nature* 302, 575–581 (1983). The genes for the antigen receptors are produced exclusively in lymphocytes through this recombinational process, which joins variable (V), diversity (D) and joining (J) gene segments. V(D)J recombination occurs at seven different loci: the immunoglobulin (Ig) heavy chain, kappa and lambda light chain loci in B lymphocytes (Tonegawa, 1983) and the T cell receptor (TCR) alpha, beta, gamma and delta chain loci in T lymphocytes (Davis, M. M. and Bjorkman, P. J. *Nature* 334, 395–402 (1988)).

The prevailing model is that a common recombinase is active in precursors of both B and T cells (Yancopoulos, G. D. et al., *Cell,* 44:251–259 (1986)), and that the sequential recombinations are executed by developmentally controlled targeting of the recombinase to the different loci (Alt, F. W., et al., *Immunol. Rev.* 89, 5–30 (1986)). The assembly process is tightly regulated, occurring in a preferred temporal order (D to J joins occur before V to D, lambda segments rearrange before kappa and in a lineage specific manner (loci recombined in T cells are never fully rearranged in B cells). Developing B cells and T cells rearrange distinct gene segment families in a well-defined temporal order. In developing B cells, the heavy chain locus is rearranged before the light chain loci. Maki, R. et al., *Science,* 209:1366–1369 (1980); Perry, R. P. et al., *Proc. Natl. Acad. Sci., USA,* 78:247–251 (1981); Alt, F. et al., *Cell,* 27:381–390 (1981); Alt, F. et al., *EMBO J.,* 3:1209–1219 (1984); Reth, M. G. et al., *Nature,* 317:353–355 (1985). In developing T cells, the $\beta$ chain locus is rearranged before the $\alpha$ chain locus. Raulet, D. H. et al., *Nature,* 314:103–107 (1985); Snodgrass, H. R. et al., *Nature,* 315:232–233 (1985); Samelson, L. E. et al., *Nature,* 315:765–768 (1985).

The complex mechanisms regulating V(D)J recombination are not well understood. Rearrangements are mediated by recombination signal sequences (RSSs) that flank all recombinationally competent, V, D and J gene segments. These signals are conserved among the different loci and species that carry out V(D)J recombination and are functionally interchangeable. RSSs, necessary and sufficient to direct recombination, consist of a syad-symmetric heptamer, an AT-rich nonamer and an intervening spacer region of either 12 or 23 bp. The two spacer lengths define two different RSSs and one of each is required for efficient joining to occur.

A number of activities must be involved in the joining reaction; these include the recognition of RSSs, enconucleolytic cleavage at or near the signal border, base trimming and addition (the joints of coding sequences are imprecise) and ligation of the cleaved ends (Sakano, H. et al. *Nature,* 280:288–294 (1979); Max, E. E. et al., *Proc. Natl. Acad, Sci., USA,* 76:3450–3454 (1979); Early, P. et al., *Cell,* 19:981–992 (1980); Sakano, H. et al., *Nature,* 290:562–565 (1981); Davis, M. M., *Annu. Rev. Immunol.,* 3:537–560 (1985). Gene segments flanked by joining signals with 12 bp spacers are joined only to gene segments flanked by joining signals with 23 bp spacers. Although different sets of genes are rearranged in developing B and T cells, exogenously introduced T cell receptor gene segments can be efficiently recombined in pre-B cells. This suggests that B and T cell lineages use the same recombination machinery, as discussed by Yancopoulos, G. D. et al., (1986).

The cis-acting sequences required for V(D)J recombination have been described in detail (Tonegawa, 1983; Hesse et al., *Genes Dev.* 3, 1053–1061 (1989). A gene called the recombination activation gene RAG-1 has been isolated by virtue of its ability to activate V(D)J recombination in NIH 3T3 fibroblasts on an artificial recombination substrate carrying selectable markers (Schatz and Baltimore, 1988; Schatz, D. G., et al. *Cell* 59, 1035–1048 (1989)). A second, structurally unrelated gene called RAG-2 was later identified in the immediate vicinity of RAG-1 (Oettinger, et al., *Science* 248, 1517–1523 (1990).

A model has been proposed by Oettinger et al., (1990), in which RAG-1 and RAG-2 together are sufficient to induce V(D)J recombination in fibroblasts. The expression of both genes is concordant and restricted to cell lines displaying V(D)J recombination activity and developing lymphoid tissues (Schatz et al., 1989; Oettinger et al., 1990; Boehm, T. and Rabbitts, T. *Proc. Natl. Acad. Sci. USA* (1991); Turka et al., *Science* 253, 778–781 (1991). The only reported discordancies in their expression patterns are transcription of only RAG-1 in the central nervous system of the mouse, reported by Chun, et al., *Cell* 64, 189–200 (1991), and of only RAG-2 in the bursa of Fabricius of the chicken, reported by Carlson, et al. *Cell* 64, 201–208 (1991).

An animal model first described by Bosma et al., *Nature* 301, 527–530 (1983), for severe combined immunodeficiency (the scid mouse) has been reported that has been utilized for a number of different studies, including expression of human antibodies following injection of human lymphocytes into the mice, as described for example by McCune, J. M. *Curr. Op. Immunol.* 3, 2, 224–228 (1991). As reported by Bosma, G. C., et al., *J. ExP. Med.* 167, 1016–1033 (1988), the scid mouse, however, does produce some mouse immunoglobulin and some T cells, due to mostly aberrant rearrangements. Flow cytometric analysis of lymphoid organs reveals a blockade of lymphocyte differentiation at an immature stage, as further reviewed by Bosma, M. J. and Carroll, A. M. *Annu. Rev. Immunol.* 9, 323–350 (1991).

It is therefore an object of the present invention to produce an animal that is totally unable to produce functional immunoglobulin or T cell receptors.

It is a further object of the present invention to determine whether both RAG-1 and RAG-2 are required in vivo for expression of functional immunoglobulin and T cell receptors.

SUMMARY OF THE INVENTION

Immunodeficient animals are generated by introducing a mutation in RAG-1 into the germline of the animals via gene targeting in embryonic stem cells. In the following description, the production of RAG-1 deficient mice is detailed. RAG-1 deficient mice have no mature B and T lymphocytes. The arrest of B and T cell differentiation occurs at an early stage and correlates with the inability to perform V(D)J recombination. To date, these mice do not have mature B and T lymphocytes, nor do they express immunoglobulin or T cell receptors. The same strategy can be applied to the generation of other RAG-1 deficient animals, such as rabbits, rats, and pigs, using known techniques. These animals are all useful for the same general purposes as the scid mice, for example, cultivation of human lymphocytes for expression of human immunoglobulin. Other uses include the establishment of continuous lymphoid cell lines and, by crossbreeding with other lines of animals, the establishment of animals developing tumors for use in studying tumor cell developments and treatments.

DETAILED DESCRIPTION OF THE INVENTION

Figure 1:
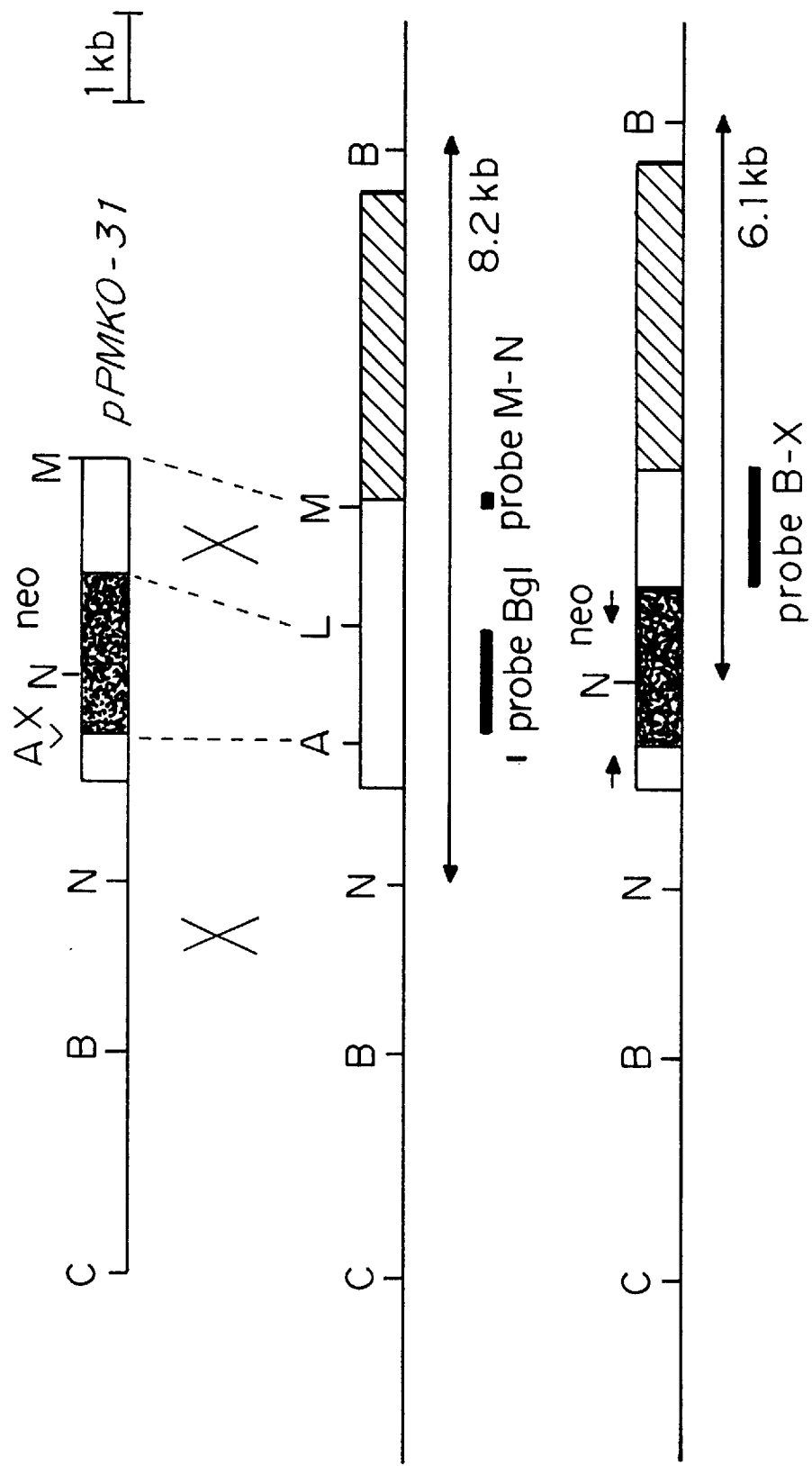
FIG. 1: Targeting Scheme: (a) Targeting vector pPMKO-31. Open box: translated RAG-1 sequences; dark box: neo selectable marker. (b) Genomic structure of the RAG-1 locus. Hatched box: untranslated RAG-1 sequences. Probes are: Bgl, for deleted sequences, as shown in FIG. 2B; and M-N, external probe for screening of the ES clones. The size of BamHI-NcoI genomic restriction fragment hybridizing to probe B-X is indicated below the double-arrowed line; and (c) Consequence of homologous integration. 1356 bp of sequences at the 5' end of RAG-1 are deleted. The transcription of neo gene is in the opposite orientation of RAG-1 (indicated with arrows). The 8.1 kb BamHI-NcoI genomic restriction is replaced by a 6.2 kb fragment recognized on Southern blot by using probe B-X, as shown in FIG. 2A. Abbreviations for restriction sites: C, Cla1; A, Apa1; X, Xho1; L, Bgl1; B, BamHI; N, NcoI; M, Mlu1.

It has been discovered that it is possible to produce a severely combined immunodeficient animal by inactivating the RAG-1 or RAG-2 gene in the animal. Although initial in vitro evidence was unclear whether both the RAG-1 and RAG-2 genes were required for production of immunoglobulin and TCR, it has now been determined that both genes must be expressed to yield functional recombinases for the animal to be fully immunocompetent. As described in detail below with reference to the production and characterization of a mutant mouse containing a deletion in the RAG-1 gene, any animal can be constructed in a similar fashion by inactivation of the RAG-1 or RAG-2 gene. There are differences, however, in the two genes which require that the two genes be dealt with on an individual basis and one cannot extrapolate from one gene to the other.

As described below, a deletion was introduced into the RAG-1 gene, shown below, of pluripotent embryonic stem (ES) cells, as described by Evans, M. J., and Kaufmann, M. H. *Nature* 292, 154–156 (1981), using the targeted gene disruption technique of Capecchi, M. R. *Science* 244, 1288–1292 (1989), in order to produce mice homozygous for the RAG-1 mutation (hereafter called homozygous, mutant or RAG-1 deficient mice, or homozygotes) resulting in expression of a non-functional recombinase.

Although described with specific reference to a mouse, the same techniques can be used to produce other animals, or cell lines derived from other animals or humans, which are deficient in RAG-1.

Although the example uses a substantial deletion of the gene to produce a non-functional recombinase, any alteration which would make the RAG-1 gene encode a non-functional recombinase, or interfere with expression of the gene, such as the addition, deletion, substitution, or modification of one or more bases of the gene or the sequences controlling its expression, could be used. These alterations include insertion of the neo gene, or other DNA sequences, into the RAG-1 gene, thereby interrupting the gene, frameshift mutations, other deletions in or around the gene, and mutations of the RAG-1 promoter, enhancer, or splice sites (donor and acceptor).

The RAG-1 gene sequence is described in Schatz, et al., *Cell* 59, 1035–1048 (1989), the teachings of which are incorporated herein. The nucleotide sequence (Sequence I.D. No. 1) and the amino acid sequence (Sequence I.D. No. 2) are appended hereto.

See also Tybulewicz, et al., *Cell* 65, 1153–1163 (1991) and Adra, et al., *Gene* 60, 65–74 (1987).

The RAG-1 deficient mice produced in the following example do not have any mature B and T lymphocytes. Flow cytometric analysis of lymphoid organs reveals a blockade of lymphocyte differentiation at an immature stage, similar to the situation of the scid mouse, described by Bosma and Carroll (1991). Southern blot analysis of DNA from thymus and bone marrow-derived Abelson-transformed cell lines indicates that both Ig and TCR gene loci remain in the germline configuration.

A similar phenotype is described in RAG-2 deficient mice by Shinkal et al., *Cell* (in press, 1992). If either RAG-1 or RAG-2 gene is inactivated, the animal does not contain mature lymphocytes. Taken together, these data suggest that RAG-1 and RAG-2 are both necessary in vivo to either activate or catalyze the V(D)J recombination reaction.

The availability of the RAG-1 deficient animals facilitates many basic and applied research projects.

The RAG-1 mutant mice are a useful alternative to the scid mouse. In addition to leakiness, discussed in more detail below, the scid mouse has at least two other drawbacks compared to the RAG-1 mutation: the genetic defect has not been characterized and the mutation is known to affect other processes such as double-strand break-related DNA-repair, as reported by Fulop et al., *Nature* 347, 479–482 (1990); Hendrickson et al., *Proc. Natl. Acad. Sci. USA* 88, 4061–4065 (1991). The RAG-1 mouse or other RAG-1 deficient animals can be used for any application the scid mouse is used for.

Other proposed uses for the RAG-1 deficient, or mutant, animals:

Lymphopoiesis:

The rearrangement of antigen receptor genes is thought to be preceded by the commitment of hemopoietic progenitor cells first to lymphoid cell development and then to the progenitor of the three major lymphocyte classes, $\alpha\beta$ T cells, gamma-delta T cells and B-cells. In RAG-1 deficient mice, such progenitors could accumulate and be used to establish continuous cell lines. Transfection of the cell lines with the intact RAG-1 gene can reveal their commitment to one or more of the major lymphocyte classes. The lines will be useful to study the effect of the known cytokines and to identify putative new factors which regulate the growth and differentiation of these cells. The information obtained may be exploited to improve the recovery of the immune system after human bone marrow transplantation.

Leukemogenesis or development of lymphomas

The differentiation arrest of lymphoid progenitor cells in RAG-1 deficient mice is expected to lead to the development of leukemias or lymphomas. Such tumors have not yet been observed in RAG-1 deficient mice but might occur at high frequency if activated oncogenes or tumor suppressor gene defects are introduced in these mice by breeding with transgenic mice or other mutant mice. Such studies may increase the understanding of lymphoid tumor cell development and perhaps lead to new approaches to therapy.

Transplantation of human hemopoietic cells or tissues

Various groups have transplanted human blood cells, human progenitor cells or fragments of human fetal liver, thymus and lymph nodes to immunodeficient SCID or xid/beige/nude mice. Because of the complete absence of T- and B-cells, RAG-1 deficient mice are preferable as recipients. If necessary, the deficient animals can be additionally depleted of NK cells by breeding with beige mice or by treatment with anti-asialo GM1 antibodies. There are many potential applications of such mice. For example:

The RAG-1 deficient animals are useful in studies of human hemopoietic cells, such as in the identification of progenitor cells including lymphoid progenitors and pluripotential stem cells; in the identification of new cytokines which play a role in the growth and differentiation of human hemopoietic cells; in the analysis of the effect of known cytokines; and in the analysis of drugs on human hemopoietic cells.

The RAG-1 deficient animals are also useful in studies on pathogenetic mechanisms in diseases caused by lymphotropic viruses such as human immunodeficient virus (HIV), human T lymphotropic virus (HTLV-1) or Epstein Barr virus (EBV), and in the course of determining new therapeutic approaches.

The RAG-1 deficient animals are also useful in studies of defense mechanisms against microorganisms that cause diseases in immunocompromised patients such as cytomegalovirus, pneumocystis carinii or candida.

The RAG-1 deficient animals should be useful in the preclinical evaluation of "gene therapy". Genes may be introduced into hemopoietic progenitor cells, preferably into pluripotential stem cells with self-renewal capacity from patients with inherited genetic defects. The transfected cells can be kept frozen until their suitability for clinical use has been demonstrated in the RAG-1 deficient animals.

EXAMPLE 1

Generation of the Mutation in RAG-1 in ES Cells and in Mice

Construction of Targeting Vector

RAG-1 was cloned by screening a genomic EMBL-3 phage library prepared from D3 embryonic stem cells (Gossler et al., Proc. Natl. Acad. Sci. USA 83, 9065–9069 (1986)) (gift from Alcino Silva) with a probe generated by the polymerase chain reaction (PCR) technique (gift from Asa Abeliovich). One positive phage out of 1.2 million plaques screened was purified and mapped by restriction enzyme analysis. A 9 kb Cla1 and a 6.5 kb BamHI-Cla1 fragment were subcloned into pBluescript/SK— (Stratagene) and further mapped. The targeting vector pPMKO-31 was constructed in a quatrimolecular ligation reaction, using a 6 kb ClaI-ApaI fragment upstream of the RAG-1 coding sequence (ending at position 482), a 1.8 kb fragment containing the pgk-neo gene (Adra, et al., 1987) (gift from Michael A. Rudniki) excised with ApaI and BamHI, a 1277 bp BglI-MluI fragment containing sequences between positions 1837 and 3113, and the plasmid pGEM7 (Promega) cut with ClaI and MluI. This targeting vector is designed to delete 1356 nucleotides of the RAG-1 coding sequence between positions 482 and 1837 and replace it with the pgk-neo gene, transcribed in the opposite orientation. The source of the pgk-neo gene is the plasmid pKJ1, described in Tybulewicz, 1991.

Targeting Experiment

ES cells were grown on mitomycin C or gamma-irradiated primary embryonic fibroblasts, and during the selections on G418-resistant fibroblasts isolated from transgenic embryos carrying a neo-resistance gene (Gossler et al., 1986). The medium composition was as described in Robertson, E. J. "Embryo-derived stem cell lines" in: Teratocarcinomas and embryonic stem cells: A practical approach. E. J. Robertson, ed. 71–112 (Oxford-Washington, D.C.: IRL Press, 1987). About $5 \times 10^7$ AB1 (McMahon, A. P., and Bradley, A. Cell 62, 1073–1085 (1991)) embryonic stem cells were electroporated with 75 $\mu$g of Mlu1 linearized pPMKO-31 using a Bio-Rad gene pulser set at 800 Volt and 3 $\mu$Farad. Selection was initiated 20 hours later at a concentration of 125 to 150 $\mu$g/ml active concentration of G418 (Gibco). Colonies were picked from day 6 to day 9 of selection into 96 or 24 well dishes (Costar) and expanded. Half of a 24 well was frozen down and the other half used to isolate DNA for Southern blot analysis. The colonies were screened individually by cutting genomic DNA with Xho1 and BamHI and probing the Southern blots with the external probe M-N, a 268 bp fragment containing RAG-1 coding sequence between positions 311 and 3380 (Schatz, et al., 1989).

The targeting vector pPMKO-31 (FIG. 1) was constructed from a RAG-1 genomic clone isolated from a genomic DNA library made from ES cells of a 129/Sy mouse, in order to maximize homology between the targeting plasmid and the target sequences. Homologous integration would create a deletion of 1356 basepairs in the 5' end of the coding sequence of RAG-1. The resulting mutation would most likely be a null mutation, as the deletion encompasses about half of the coding sequence of RAG-1 and includes the putative nuclear localization signal and zinc-finger-like motif (Schatz et al., 1989). Moreover, as the neo-selectable marker is introduced in the opposite transcriptional orientation, a polypeptide correctly initiated at the translation start site would probably be prematurely terminated at the level of the neo-gene.

The targeting strategy was to isolate a number of G418-resistant clones and analyze them individually, since previous experience had shown that the negative selection step utilizing the HSV-thymidine kinase gene (Mansour et al., Nature 336, 348–352 (1988)) did not give a significant enrichment and that targeting frequencies among the G418-resistant clones are generally high enough for direct screening.

Using AB1 embryonic stem cells (McMahon et al), targeted clones were obtained in two independent experiments, one (clone A103) out of 130 G418-resistant clones in one experiment and one (clone G113) out of 117 clones in another experiment.

Generation of Chimeric Mice

Litters from heterozygous mice were from birth housed in autoclaved micro-isolator cages and given autoclaved food and water.

Chimaeras were produced as described in Bradley, 1987, the teachings of which are incorporated herein. Clone A103 was injected in C57BL/6 blastocysts. From those implanted females that became pregnant (representing 194 implanted blastocysts), 29 male, 1 hermaphrodite and 15 female chimaeras were born, with an average coat color chimerism of about 75%. Of 27 chimeric males that were test mated to CD1 or C57BL/6 females, 17 had live offspring and 12 were germline chimaeras. One out of eight female chimaeras had germline offspring. Clone A103 was injected in eight Balb/c blastocysts, which gave rise to two male and one female chimaeras. This female proved to be a germline chimeric. Clone G113 did not give rise to good chimaeras.

Screening of Mice

Mice were screened by Southern blot analysis on genomic DNA isolated according to Laird et al., 1991. The DNA samples were cut with Pst 1 or a combination of BamHI and Nco1 and the Southern blots were probed with probe B-X, a 1544 bp fragment containing RAG-1 coding sequences between positions 1837 and 3380 (Schatz et al., 1989). Southern blots were exposed using a Fujix Bio-Image Analyzer BAS2000.

(129/Sv×CD1) F1 heterozygotes were intercrossed to produce homozygotes. Offspring was genotyped by Southern blot analysis of tail DNA. Data from one litter was analyzed by Southern Blot on tail DNA. Tail DNA was isolated from a litter of 13 mice of a (129/Sv×CD1) F1 heterozygote intercross. DNA was cut with BamHI and Nco1, and hybridized to probe B-X. The upper band indicates the wild type allele, the lower band corresponds to the allele that has undergone homologous recombination. Three mice in the litter are homozygous, as they have only the lower band. The blot was stripped and hybridized with probe Bg1, which is complementary to sequences within the deletion generated by the targeting event. The three homozygous mice do not contain DNA sequences hybridizing to this probe. Of 20 newborn animals, 6 were homozygous, and 33 out of 112 offspring genotyped after weaning were homozygous.

Flow Cytometric Analysis $10^5$ to $10^6$ cells were preincubated in 96 well round bottom dishes (Costar) for 20 minutes in 12.5 $\mu$l containing 5 $\mu$l of staining solution (composed of PBS/0.1% sodium azide/1% fetal calf serum), and 2.5 $\mu$l of each normal hamster, normal mouse (Jackson Immunology) and normal rat serum (Caltag). The preincubation with serum was omitted in the stainings with goat-antimouse. The samples were then stained by adding another 12.5 $\mu$l of staining solution containing 0.25 $\mu$l of antibodies, either biotinylated or conjugated with fluorescein isothiocyanate (FITC) or phycoerythrin (PE). The antibodies used were: 2C11 for CD3-epsilon (Pharmingen), H57-597 for TCR alpha beta (Pharmingen), 53-6.7 for CD8 (Becton Dickinson), GK1.5 for CD4 (Pharmingen), 53-2.1 for Thy1.2 (Pharmingen), PC 61 5.3 for 1L2-receptor/CD25 (gift from Kunio Sano), goat-antimouse immunoglobulin (Caltag), RA3-6B2 for B220 (Boehringer Mannheim), 53-7.3 for CD5 (gift from Pablo Pereira), J11d (gift from Pablo Pereira), anti-Sca-1 (gift from Peggy Goodell), and M1/70 for Mac1 (Boehringer Mannheim).

Cells were stained for 30 minutes, washed twice with staining solution, incubated in 25 $\mu$l of staining solution containing streptavidin-biotin (Southern Biotechnology) at a 1:200 dilution, washed once in staining solution, once in PBS containing propidium-iodide and finally resuspended in 200 $\mu$l of PBS. Cells were kept on ice during the staining procedure and spun in a refrigerated centrifuge. Flow cytometric analysis was carried out with a Becton Dickinson FACScan using FACScan software. Dead cells were gated out by means of propidium iodide staining. 5000 to 17000 events were acquired using a large gate and the lymphoid population was analyzed with a narrower gate based upon forward scatter and side scatter.

Southern and Northern Blot Analysis

TCR $\alpha$ and $\delta$ rearrangements were analyzed by cutting genomic DNA from thymus with EcoRI and hybridizing with the 3'$J_{\delta 1}$ probe described in Chien et al., 1987 (gift from Yo-Ichi Shinkai). TCR $\beta$ rearrangements were analyzed by hybridizing with a 5'$D_1$ probe, a 1.2 kb Pst1 fragment isolated from cosmid 2.3 W7 (Malissen et al., 1984). The TCR $\alpha$ probe was a 0.6 kb BglII-BamHI fragment (Mombaerts et al., 1991). Immunoglobulin heavy chain rearrangements were analyzed by cutting with EcoRI and hybridizing with a 1.9 kb BamHI-EcoRI $J_H$ probe (Sakano et al., 1980).

The RAG-2 probe is a 246 bp fragment cloned into pUC12 with the following PCR primers: 5' ATGTCCCTG-CAGATGGTAACA 3' (position 156 to 176 in Oettinger et al., 1990) and 5' GCCTTTGTATGAGCAAGTAGC 3' (position 401 to 381 in Oettinger et al., 1990). The lambda5 (Sakaguchi and Melchers, 1986) cDNA probe was a gift from Gene Oltz.

Macroscopic Analysis

Mice homozygous for the RAG-1 mutation are healthy and indistinguishable from their normal littermates by visual inspection, up to at least 21 weeks of age, preferably maintained in a germ free environment. Two twelve old mutant males could readily fertilize either a homozygous or heterozygous mutant female. In the former case, twelve pups were born and in the latter, eleven pups. Both litters were raised successfully to weaning.

The number of cells in the lymphoid organs of twelve mutant mice of varying ages (newborn and three to nine week old mice) were determined and cared with corresponding wild-type or heterozygous littermates. The thymus of the RAG-1 deficient mice contained 15 to 130 times less cells than the thymus of the wild-type or heterozygous littermates. One four week old mutant mouse had the highest number of thymocytes among all mutant mice examined but that was still $3.4\times10^6$ compared to $230\times10^6$ thymocytes in a wild-type littermate. The numbers of non-erythroid cells in the spleen of mutant mice of three weeks or older were between five and nine times smaller than those in corresponding wild-type or heterozygous littermates. Visual inspection revealed a stroma-like structure in the site where the inguinal lymph nodes are located, but only a few non-erythroid cells, if any, could be recovered from these structures. No other obvious anatomical alterations were observed.

For histology of the brain, mice were deeply anesthetized with avertin, perfused for 2 minutes with phosphate buffered saline and then with 4% paraformaldehyde in phosphate buffer (0.1M, pH 7.4) for 15 minutes. Following perfusion the brain was removed from the skull and stored in fresh paraformaldehyde overnight at 4° C. The brains were bisected at the midline and embedded in polyester wax (polyethylene glycol distearate 400) according to the protocol of Mullen (1977). Serial ten micron sections were collected, mounted on gelatinized slides and stained with cresyl violet.

As far as a potential neurological deficit is concerned, based on the report by Chun et al., (1990), no obvious clinical symptoms have been observed to date. The mutant mice are active, have a firm grip with their forelimbs, can hear sounds, can walk on a pencil, can sense heat and feel pain and can swim as well as their heterozygous or wild-type littermates.

Absence of Mature B and T Lymphocytes

Cells from thymus, spleen, lymph nodes, bone marrow and blood were subjected to flow cytometric analysis. The thymus isolated from four, five, or seven week old mice were analyzed by FACScan. The Forward scatter (FSC) horizontally, reflects the size of the cells; side scatter (SSC) vertically, corresponds to the granularity of the cells. The thymocytes of mutant mouse are shifted to higher scatter values. Analysis with CD3 (FITC) horizontally and pan-TCR αβ (PE) vertically demonstrates that no CD3 or TCR αβ thymocytes exist in the mutant thymus. Analysis with CD8 (FITC) horizontally and CD4 (biotin-PE) vertically demonstrates that no CD8 CD4 double positive cells are observed in the mutant mouse thymus. Analysis with Thy 1.2F (FITC) horizontally and IL2-receptor/CD25 (biotin-PE) vertically demonstrates that most thymocytes in the mutant mouse express the IL2-receptor.

The spleen and bone marrow were also analyzed by FACScan using samples from the same mice. A narrow gate was used on the splenocytes to visualize only the lymphoid cells, representing 72% of the non-erythroid cells in the wild-type mouse, and 32% in the mutant mouse. Analysis with IgM (FITC) horizontally and B220 (PE) vertically show that only B220 single positive cells exist in the mutant mouse. Even in the ungated population no B220-IgM double positive cells are found. Based on the control mouse, a narrow gate on the lymphoid population was used to examine bone marrow (21% of the total cells in the RAG-1 heterozygous mouse, and 13% of the total cells in the mutant mouse). Only dull B220 single positive cells are observed in the mutant mouse.

The thymocytes of the RAG-1 deficient mouse are larger than those of wild-type or heterozygous mice, as indicated by the increased forward scatter. No CD3 positive or TCR αβ positive cells have been observed. The thymocytes are CD8-CD4 double negative and almost all of them are IL2-receptor positive (FIG. 3D). Finally, they are Thy1 positive (FIG. 3d), bright J11d positive, bright Sca-1 positive and CD5 negative. Thus, thymocyte development seems to be arrested at an immature stage.

The spleen does not contain any mature B cells as judged by the lack of staining by anti-IgM or anti-IgD antibody. About one third of the splenocytes (on a narrow gate for the lymphoid population) are B220 positive and may represent an early stage of B cell differentiation. A small fraction of the splenocytes is Mac-1 positive and could be macrophages, natural killer cells, or neutrophils. Likewise, the bone marrow contains no mature, IgM or IgD positive cells. About one fourth of the bone marrow cells, with a narrow gate on the lymphoid population are B220 positive and could be early B-cell precursors. The intensity of the B220 staining is lower than the majority of the B220 positive cells in the bone marrow of the normal mouse. The composition of the lymphoid population in the lymphoid organs of the RAG-1 deficient mouse is similar to that of the scid mouse described by Bosma and Carrol, (1991). The serum IgM levels of seven mutant mice of five to sixteen weeks have also been measured by ELISA. IgM was non detectable. The serum IgM level is a sensitive indicator for leakiness in the case of the scid mouse.

In summary, no mature B or T lymphocytes have been observed in the lymphoid organs of twelve RAG-1 deficient mice of up to the age of nine weeks and no serum IgM was detectable in mice up to the age of sixteen weeks.

Establishment of Abelson-Transformed Lines

The Abelson murine leukemia virus was used to transform bone marrow cells from a five week old female mutant mouse as well as from a wild-type female littermate, as described in Rosenberg and Baltimore, 1976. Transformation efficiency was determined by counting the number of colonies in soft agar per $10^6$ infected bone marrow cells.

A similar number of cell lines grew up in both mice. Transformation efficiency was $1.19 \times 10^{-4}$ for homozygote and $8.74 \times 10^{-5}$ for wild-type, as has been reported for scid mouse, Fulop, et al., *Cell Immunol.* 113, 192–201 (1988). All of the Abelson retrovirus-transformed lines are B220 positive and contain RAG-2 and lambda5 (Sakaguchi and Melchers, 1986) RNA (FIG. 5a and c). It is therefore likely that these cell lines originated from immature B cells. It is therefore likely that these cell lines originated from immature B cells. Mutant RAG-1 transcripts are present in all of the cell lines established from mutant mouse as determined by Northern blot analysis of expression of RAG-2, RAG-1 and lambda5 in bone marrow-derived Abelson-transformed lines. RNA was isolated from individual Abelson-lines. The blot was hybridized to (A) a RAG-2 probe (48 hr exposure); (B) the RAG-1 probe B-X (12 hr exposure); (C) a lambda5 cDNA probe (6 hr exposure); (D) a 1.5 kb AvaI-BamHI fragment from the human β-actin gene. Thirteen Abelson-lines from RAG-1 deficient mouse were analyzed; three Abelson-lines from wild-type littermate were analyzed. The cell line represented by one Abelson-line from a wild-type littermate gave neither a RAG-1 nor a RAG-2 RNA band. This is not unusual because large variations in the levels of RAG-1 and RAG-2 RNA in Abelson-transformed lines from normal mice have been observed.

In order to confirm that the absence of mature B and T lymphocytes is due to a defect in V(D)J recombination, Southern blot analysis was performed with DNA from the thymus and the Abelson-transformed lines. The $3'J_{\delta 1}$ probe described by Chien, et al., (1987), allows the analysis of rearrangements involving $D_{\delta 2}$ or $J_{\delta 1}$ and all $V_\alpha$-$J_\alpha$ rearrangements (in the latter case the $TCR_\delta$ locus is deleted). DNA from $5 \times 10^5$ cells was cut with EcoRI. The Southern blot was hybridized to the 3'Jδ1 probe. The size of the germline fragment is 7.5 kb. AB1 embryonic stem cells; thymocytes from a four week old wild-type mouse; thymocytes from a homozygous mutant mouse that is a littermate of the wild-type mouse; thymocytes from a seven week old wild-type mouse; thymocytes from a homozygous mutant mouse that is a littermate of the wild-type mouse; thymocytes from a seven week old scid mouse were compared. There is no evidence for rearrangements in the thymus of the mutant mouse. The scid mouse has two faint bands which probably represent D-D or D-J rearrangements. The blot was stripped and hybridized to the 5'Dβ1 probe. No rearrangements are observed in the thymocytes from a homozygous mutant mouse that is a littermate of the wild-type mouse or the thymocytes from a homozygous mutant mouse that is a littermate of the wild-type mouse, and no signal is visible at the level of the germline band as the DNA sequences complementary to this probe are deleted (V-D-J rearrangement) or have an altered size (D-J rearrangement). A faint band is visible in the scid thymus and probably corresponds to a D-J rearrangement. The blot was stripped again and hybridized to a TCR $C_\alpha$ probe. The intensity of the bands serves to control for variations in amount of DNA loaded and Southern transfer efficiency.

In summary, thymus DNA isolated from four and seven week old RAG-1 deficient mice showed no rearrangements, whereas thymus DNA of a seven week old scid mouse showed a low level rearrangements which are presumably aberrant, Carroll and Bosman (1991). Using a 5' $D_{\beta 1}$ probe no rearrangements were observed at the TCR β locus, whereas the scid thymus shows a faint additional band which probably represents a D-J rearrangement, as described Malissen, et al. (1984). A TCR $C_\alpha$ probe was used as a control for loading and Southern transfer efficiency of the DNA samples.

The bone marrow-derived Abelson-transformed lines were similarly analyzed with an IgJ$_H$ probe. Southern blot analysis of endogenous IgH rearrangements in bone marrow-derived Abelson-transformed lines was performed. DNA was isolated from individual Abelson-lines and cut with EcoRI. The blot was hybridized with a 1.9 kb BamHI-EcoRI fragment containing J$_{H3}$ and J$_{H4}$, using the method of Sakano et al., Nature 286, 676–683 (1980). C57BL/6 liver; Abelson-lines derived from bone marrow of a five week old RAG-1 mutant mouse; and Abelson-lines derived from bone marrow of a wild-type littermate were compared. All of the cell lines revealed a germline configuration, but none of the lines derived from the wild-type mouse retained the IgH locus in a germline configuration.

In conclusion, the inability to perform V(D)J recombination is the most likely explanation for the absence of mature B and T lymphocytes.

Histological Analysis of the Brain

In light of the reported presence of the RAG-1 transcript in the brain of the mouse (Chun et al., 1991), the brain was analyzed by histological means, although no obvious behavioral deficit was observed. Brains of seven and eight week old homozygous and wild-type littermates were analyzed with serial sagittal sections stained with cresyl violet.

No significant defect could be found in the structure of the brains of the mutant mice when compared to control littermates. On gross examination all major external features of the RAG-1 deficient brain were normal, including its size and the relative placement of the various fissures and nerve roots. Histological exam revealed that, to a first approximation, most major nuclei found in the wild type littermate were present in the mutant mouse and were normal in size and cellular appearance. No structural alterations were observed.

Particular attention was focused on the hippocampus and the cerebellum as these are the two regions that are believed to have the highest levels of RAG-1 expression by in situ hybridization, as reported by Chun, et al., (1991). Comparison of wild-type with mutant shows a nearly identical pattern of foliation of the cerebellar cortex. Similarly the macro-architecture of the hippocampus is unaltered in the mutant mouse. High magnification views of both cerebellum and hippocampus reveal no distortion of the micro-architecture of the mutant compared to the wild type brain. As these areas both are sensitive indicators of pattern alterations, as described by Nowakowsky (1984) and Joyner, et al., (1991), their normal appearance in the mutant suggest that the absence of RAG-1 function does not interfere in a major way with developmental events such as neurogenesis, migration and differentiation.

There was near identity in the foliation pattern of the cerebellar cortex and the close congruence of the structure of the hippocampi. Higher magnification of cerebellar cortex reveals no alternation in the density or Nissl morphology of cells in the molecular, Purkinje or granule cell layer between wild type and mutant. Likewise, the cytoarchitecture of the hippocampus is indistinguishable in wild-type and mutant brains (270×).

RAG-1 and RAG-2 Are Both Required for V(D)J Recombination

The generation and the initial analysis of mice with a mutation of the RAG-1 gene, which has been implicated in the regulation or the catalysis of V(D)J recombination (Schatz et al., 1980), show that this gene is necessary in vivo for V(D)J recombination to occur. The presence of RAG-2 (Oettinger et al., 1990) transcripts in the Abelson-transformed lines derived from the RAG-1 mutant mouse indicates that the mutation introduced in the RAG-1 gene did not inhibit expression of the closely linked RAG-2 gene. RAG-1 transcripts of a slightly larger size are observed in the RAG-1 deficient lines but are not likely to give rise to any functional protein. Taken together with the data on the RAG-2 deficient mice described by Shinkal et al., Cell (in press 1992), the results support the hypothesis that both the RAG-1 and RAG-2 gene products are required in vivo for V(D)J recombination.

Immature B and T Cells

Flow cytometric analysis of cells from lymphoid organs reveals the absence of mature B and T lymphocytes, which is most likely the result of the deficit in V(D)J recombination. B and T cell precursors need to produce functional antigen receptors on their surface in order to produce a T cell receptor do not undergo the process of positive selection. Thus, like in the scid mouse, the thymus of the RAG-1 mutant mouse remains small and contains immature, large, CD8 CD4 double negative thymocytes expressing the IL2-receptor. Likewise, the bone marrow and the spleen of the RAG-1 mutant mouse contain a population of dull B220 positive cells, a fraction of which may represent pre-B cells. Some of these cells may serve as targets for transformation by the Abelson retrovirus.

No Leakiness

The combination of the flow cytometric data, Southern blot analysis and serum IgM ELISA measurements revealed no leakiness in the phenotype to date.

The observations made to date are in contrast to those in the scid mouse. Using the 3'J$_{\delta 1}$ probe of Chien, et al., (1987), D-J rearrangements at the TCR δ locus have been reported for scid mice by Carroll and Bosma, (1991). As these mice grow older, some B and T cells express a functional antigen receptor and form an oligoclonal repertoire (Carroll and Bosma, 1988; Bosma, et al., 1988; Carroll, et al., 1989; Bosma and Carroll, 1991). As these mice grow older, some B and T cells express a functional antigen receptor and form an oligoclonal repertoire. This leakiness is partly the result of reversion of the mutation in individual lymphocyte progenitors. As a result, serum levels of IgM increase in scid mice as they age.

Modifications and variations of the mutant animals, and methods of making and using them, will be obvious to those skilled in the art from the foregoing detailed description of the invention, and are intended to fall within the following claims.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 3342 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Mouse ( x i ) SEQUENCE DESCRIPTION: SEQ ID NO:1:

```
TTGCTATCTC  TGTGGCATCG  AGTGTTAACA  ACCAAGCTGC  AGACATTCTA  GCACTCTGGC    60
CGGGAGGCCT  GTGGAGCAAG  GTAGCTTAGC  CAACATGGCT  GCCTCCTTGC  CGTCTACCCT   120
GAGCTTCAGT  TCTGCACCCG  ATGAAATTCA  ACACCCACAA  ATCAAATTTT  CCGAGTGGAA   180
ATTTAAGCTG  TTTAGGGTGA  GATCCTTTGA  AAAGGCACCC  GAAGAAGCAC  AGAAGGAGAA   240
GGATTCCTCA  GAGGGGAAAC  CTTACCTAGA  ACAGTCTCCA  GTAGTTCCAG  AGAAGCCTGG   300
TGGTCAGAAC  TCAATTCTGA  CTCAACGAGC  ACTGAAACTC  CATCCTAAAT  TTTCAAAGAA   360
ATTCCATGCT  GATGGGAAGT  CAAGCGACAA  AGCAGTTCAC  CAAGCCAGGC  TTAGACACTT   420
CTGCCGCATC  TGTGGGAATC  GTTTCAAGAG  TGACGGGCAC  AGCCGGAGAT  ACCCAGTCCA   480
CGGGCCCGTG  GACGCTAAAA  CCCAAAGTCT  TTTCCGAAAG  AAGGAAAAAA  GAGTCACTTC   540
CTGGCCAGAC  CTCATTGCCA  GGATTTTCCG  GATCGACGTG  AAGGCAGATG  TTGACTCCAT   600
CCACCCGACG  GAATTCTGCC  ATGACTGTTG  GAGCATCATG  CACAGAAAGT  TCAGCAGTTC   660
CCACAGTCAG  GTCTACTTCC  CAAGGAAAGT  GACCGTGGAG  TGGCACCCCC  ACACACCGTC   720
CTGTGACATC  TGTTTTACTG  CCCATCGGGG  ACTCAAGAGG  AAGAGACATC  AGCCCAATGT   780
GCAGCTCAGC  AAGAAACTAA  AAACTGTGCT  CAACCACGCG  AGACGGGACC  GTCGCAAGAG   840
AACTCAGGCT  AGGGTCAGCA  GCAAGGAAGT  CCTGAAGAAG  ATCTCCAACT  GCAGTAAGAT   900
TCATCTCAGT  ACCAAGCTTC  TTGCCGTGGA  CTTCCCAGCA  CACTTTGTGA  ATCCATCTC    960
CTGCCAGATA  TGCGAACACA  TTCTGGCTGA  TCCCGTGGAG  ACCAGCTGCA  AGCATCTATT  1020
CTGTAGGATC  TGCATTCTCA  GATGTCTCAA  AGTCATGGGC  AGCTATTGTC  CCTCTTGCCG  1080
ATATCCGTGC  TTCCCTACTG  ACCTGGAGAG  CCCAGTGAAG  TCCTTTCTGA  ACATCTTGAA  1140
TTCTCTCATG  GTCAAGTGTC  CCGCGCAAGA  TTGCAATGAG  GAAGTGAGTC  TGGAAAAATA  1200
TAACCACCAT  GTGTCAAGCC  ACAAAGAATC  TAAAGAGACT  TGGTGCATA   TCAATAAAGG  1260
GGGACGGCCT  CGCCAGCATC  TCCTGTCACT  GACGAGAAGG  GCGCAGAAAC  ATCGGCTGAG  1320
GGAGCTCAAG  ATTCAAGTCA  AAGAATTTGC  TGACAAAGAA  GAAGGTGGAG  ATGTGAAGGC  1380
TGTCTGCTTG  ACATTGTTTC  TCCTGGCACT  GAGGGCGAGG  AATGAGCACA  GGCAAGCTGA  1440
TGAATTAGAG  GCCATCATGC  AAGGCAGGGG  CTCCGGGCTT  CAACCAGCTG  TTTGCTTGGC  1500
CATCCGTGTC  AATACCTTCC  TCAGCTGTAG  CCAATACCAT  AAGATGTACA  GGACTGTGAA  1560
AGCTATCACT  GGGAGGCAGA  TTTTTCAACC  TTTGCATGCT  CTTCGGAATG  CCGAGAAAGT  1620
CCTTCTGCCA  GGCTACCATC  CCTTTGAGTG  GCAGCCCCA   CTGAAGAATG  TGTCCTCCAG  1680
AACTGATGTT  GGAATTATTG  ATGGGCTGTC  TGGACTTGCC  TCCTCTGTGG  ATGAGTACCC  1740
AGTAGATACC  ATTGCGAAGA  GGTTCCGCTA  CGACTCTGCT  TTGGTGTCTG  CTTTGATGGA  1800
CATGGAAGAA  GACATCTTGG  AAGGCATGAG  ATCCCAAGAT  CTTGATGACT  ACCTGAATGG  1860
```

| | | | | | |
|---|---|---|---|---|---|
| TCCCTTCACA | GTGGTGGTAA | AGGAGTCTTG | CGATGGAATG | GGGGATGTGA | GTGAGAAGCT | 1920 |
| CGGGAGTGGG | CCCGCAGTTC | CAGAAAAGGC | CGTTCGTTTC | TCTTTCACAG | TCATGAGAAT | 1980 |
| TACGATAGAG | CATGGTTCAC | AGAACGTGAA | GGTGTTTGAG | GAACCCAAGC | CCAATTCTGA | 2040 |
| ACTGTGTTGC | AAGCCGTTGT | GTCTTATGCT | GGCAGATGAG | TCTGACCATG | AGACCCTTAC | 2100 |
| TGCTATTCTA | AGCCCCCTCA | TTGCCGAGAG | GGAGGCCATG | AAGAGCAGTG | AATTAACGCT | 2160 |
| GGAGATGGGA | GGCATCCCCA | GGACTTTTAA | ATTCATCTTC | AGGGGCACTG | GATACGATGA | 2220 |
| AAAACTTGTC | CGGGAAGTAG | AAGGCTTGGA | AGCTTCTGGC | TCAGTCTACA | TCTGTACACT | 2280 |
| CTGTGACACC | ACCCGTTTGG | AAGCCTCTCA | GAATCTTGTC | TTCCAGTCCA | TAACCAGAAG | 2340 |
| CCACGCCGAG | AACCTGCAGC | GCTATGAGGT | CTGGCGGTCC | AATCCGTATC | ATGAGTCCGT | 2400 |
| GGAAGAGCTC | CGGGACCGGG | TGAAAGGGGT | CTCTGCCAAA | CCTTTCATCG | AGACAGTCCC | 2460 |
| TTCCATAGAT | GCGCTTCACT | GTGACATTGG | CAATGCAGCT | GAATTCTATA | AGATTTTCCA | 2520 |
| GCTGGAGATA | GGGGAAGTGT | ATAAACATCC | CAATGCCTCT | AAAGAGGAAA | GGAAGAGATG | 2580 |
| GCAGGCCACG | CTGGACAAAC | ATCTCCGGAA | AAGGATGAAC | TTAAAACCAA | TCATGAGGAT | 2640 |
| GAATGGCAAC | TTTGCCCGGA | AGCTTATGAC | CCAAGAGACT | GTAGACGCAG | TTTGTGAGTT | 2700 |
| AATTCCTTCT | GAGGAGAGGC | ATGAAGCTCT | CAGGGAGCTC | ATGGACCTTT | ACCTGAAGAT | 2760 |
| GAAACCCGTG | TGGCGCTCTT | CATGTCCCGC | TAAAGAGTGT | CCAGAGTCCC | TCTGTCAGTA | 2820 |
| CAGTTTCAAC | TCACAGCGTT | TCGCGGAACT | CCTCTCCACC | AAGTTCAAAT | ATAGATACGA | 2880 |
| GGGCAAAATC | ACCAATTACT | TTCACAAAAC | CTTGGCACAT | GTCCCTGAAA | TTATTGAAAG | 2940 |
| GGATGGCTCT | ATCGGGGCCT | GGGCAAGTGA | GGGAAATGAA | TCGGGTAACA | AGCTGTTTAG | 3000 |
| ACGGTTTCGG | AAAATGAATG | CCAGGCAGTC | CAAGTGCTAT | GAGATGGAAG | ATGTCCTGAA | 3060 |
| ACATCACTGG | CTGTATACTT | CAAAATACCT | CCAGAAGTTT | ATGAATGCTC | ATAACGCGTT | 3120 |
| AAAAGCTCT | GGGTTTACCA | TGAACTCAAA | GGAGACCTTA | GGGGACCCTT | TGGGCATTGA | 3180 |
| GGACTCTCTG | GAAAGCCAAG | ATTCAATGGA | GTTTTAAATA | GGATCTCCAC | ATAGAAGTTG | 3240 |
| GTATTTGCCA | ATGTGTTTTC | CTTTGGGTTG | CAGTGAGGTC | TTCTCCTAGC | ACCTAGCACA | 3300 |
| TTGCCATGTG | GGTGGGTCTT | ATCACCCAAG | GGGTGACATG | TT | | 3342 |

(2) INFORMATION FOR SEQ ID NO:2:

(i) SEQUENCE CHARACTERISTICS:
        (A) LENGTH: 1040 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Mouse (xi) SEQUENCE DESCRIPTION: SEQ ID NO:2:

```
Met  Ala  Ala  Ser  Leu  Pro  Ser  Thr  Leu  Ser  Phe  Ser  Ser  Pro  Ala  Asp
  1             5                    10                     15

Glu  Ile  Gln  His  Pro  Gln  Ile  Lys  Phe  Ser  Glu  Trp  Lys  Phe  Lys  Leu
             20                     25                     30

Phe  Arg  Val  Arg  Ser  Phe  Glu  Lys  Ala  Pro  Glu  Glu  Ala  Gln  Lys  Glu
             35                     40                     45

Lys  Asp  Ser  Ser  Glu  Gly  Lys  Pro  Tyr  Leu  Glu  Gln  Ser  Pro  Val  Val
```

-continued

```
                    50                          55                          60

Pro  Glu  Lys  Pro  Gly  Gly  Gln  Asn  Ser  Ile  Leu  Thr  Gln  Arg  Ala  Leu
 65                      70                       75                       80

Lys  Leu  His  Pro  Lys  Phe  Ser  Lys  Lys  Phe  His  Ala  Asp  Gly  Lys  Ser
                     85                       90                       95

Ser  Asp  Lys  Ala  Val  His  Gln  Ala  Arg  Leu  Arg  His  Phe  Cys  Arg  Ile
              100                      105                      110

Cys  Gly  Asn  Arg  Phe  Lys  Ser  Asp  Gly  His  Ser  Arg  Arg  Tyr  Pro  Val
               115                      120                      125

His  Gly  Pro  Val  Asp  Ala  Lys  Thr  Gln  Ser  Leu  Phe  Arg  Lys  Lys  Glu
      130                      135                      140

Lys  Arg  Val  Thr  Ser  Trp  Pro  Asp  Leu  Ile  Ala  Arg  Ile  Phe  Arg  Ile
145                      150                      155                      160

Asp  Val  Lys  Ala  Asp  Val  Asp  Ser  Ile  His  Pro  Thr  Glu  Phe  Cys  His
                    165                      170                      175

Asp  Cys  Trp  Ser  Ile  Met  His  Arg  Lys  Phe  Ser  Ser  Ser  His  Ser  Gln
               180                      185                      190

Val  Tyr  Phe  Pro  Arg  Lys  Val  Thr  Val  Glu  Trp  His  Pro  His  Thr  Pro
          195                      200                      205

Ser  Cys  Asp  Ile  Cys  Phe  Thr  Ala  His  Arg  Gly  Leu  Lys  Arg  Lys  Arg
     210                      215                      220

His  Gln  Pro  His  Val  Gln  Leu  Ser  Lys  Lys  Leu  Lys  Thr  Val  Leu  Asn
225                      230                      235                      240

His  Ala  Arg  Arg  Asp  Arg  Arg  Lys  Arg  Thr  Gln  Ala  Arg  Val  Ser  Ser
                    245                      250                      255

Lys  Glu  Val  Leu  Lys  Lys  Ile  Ser  Asn  Cys  Ser  Lys  Ile  His  Leu  Ser
               260                      265                      270

Thr  Lys  Leu  Leu  Ala  Val  Asp  Phe  Pro  Ala  His  Phe  Val  Lys  Ser  Ile
          275                      280                      285

Ser  Cys  Gln  Ile  Cys  Glu  His  Ile  Leu  Ala  Asp  Pro  Val  Glu  Thr  Ser
     290                      295                      300

Cys  Lys  His  Leu  Phe  Cys  Arg  Ile  Cys  Ile  Leu  Arg  Cys  Leu  Lys  Val
305                      310                      315                      320

Met  Gly  Ser  Tyr  Cys  Pro  Ser  Cys  Arg  Tyr  Pro  Cys  Phe  Pro  Thr  Asp
                    325                      330                      335

Leu  Glu  Ser  Pro  Val  Lys  Ser  Phe  Leu  Asn  Ile  Leu  Asn  Ser  Leu  Asn
               340                      345                      350

Val  Lys  Cys  Pro  Ala  Gln  Asp  Cys  Asn  Glu  Glu  Val  Ser  Leu  Glu  Lys
          355                      360                      365

Tyr  Asn  His  His  Val  Ser  Ser  His  Lys  Glu  Ser  Lys  Glu  Thr  Leu  Val
     370                      375                      380

His  Ile  Asn  Lys  Gly  Gly  Arg  Phe  Arg  Gln  His  Leu  Leu  Ser  Leu  Thr
385                      390                      395                      400

Arg  Arg  Ala  Gln  Lys  His  Arg  Leu  Arg  Glu  Leu  Lys  Ile  Gln  Val  Lys
                    405                      410                      415

Glu  Phe  Ala  Asp  Lys  Glu  Glu  Gly  Gly  Asp  Val  Lys  Ala  Val  Cys  Leu
               420                      425                      430

Thr  Leu  Phe  Leu  Leu  Ala  Leu  Arg  Ala  Arg  Asn  Glu  His  Arg  Gln  Ala
          435                      440                      445

Asp  Glu  Leu  Glu  Ala  Ile  Asn  Gln  Gly  Arg  Gly  Ser  Gly  Leu  Gln  Pro
     450                      455                      460

Ala  Val  Cys  Leu  Ala  Ile  Arg  Val  Asn  Thr  Phe  Leu  Ser  Cys  Ser  Gln
465                      470                      475                      480
```

```
Tyr His Lys Met Tyr Arg Thr Val Lys Ala Ile Thr Gly Arg Gln Ile
            485             490                 495
Phe Gln Pro Leu His Ala Leu Arg Asn Ala Glu Lys Val Leu Leu Pro
            500             505                 510
Gly Tyr His Pro Phe Glu Trp Gln Pro Pro Leu Lys His Val Ser Ser
            515             520                 525
Arg Thr Asp Val Gly Ile Ile Asp Gly Leu Ser Gly Leu Ala Ser Ser
            530             535                 540
Val Asp Glu Tyr Pro Val Asp Thr Ile Ala Lys Arg Phe Arg Tyr Asp
545             550             555                 560
Ser Ala Leu Val Ser Ala Leu Met Asp Met Glu Glu Asp Ile Leu Glu
                565             570                 575
Gly Met Arg Ser Gln Asp Leu Asp Asp Tyr Leu Asn Gly Pro Phe Thr
            580             585                 590
Val Val Val Glu Glu Ser Cys Asp Gly Met Gly Asp Val Ser Glu Lys
            595             600                 605
Leu Gly Ser Gly Pro Ala Val Pro Glu Lys Ala Val Arg Phe Ser Phe
    610             615                 620
Thr Val Met Ala Ile Thr Ile Glu His Gly Ser Gln Asn Val Lys Val
625             630                 635                 640
Phe Glu Glu Pro Lys Pro Asn Ser Glu Leu Cys Cys Lys Pro Leu Cys
            645             650                 655
Leu Asn Leu Ala Asp Glu Ser Asp His Glu Thr Leu Thr Ala Ile Leu
            660             665                 670
Ser Pro Leu Ile Ala Glu Arg Glu Ala Met Lys Ser Ser Glu Leu Thr
            675             680                 685
Leu Glu Met Gly Gly Ile Pro Ala Thr Phe Lys Phe Ile Phe Arg Gly
            690             695                 700
Thr Gly Tyr Asp Glu Lys Leu Val Arg Glu Val Glu Gly Leu Glu Ala
705             710             715                 720
Ser Gly Ser Val Tyr Ile Cys Thr Leu Cys Asp Thr Thr Arg Leu Glu
                725             730                 735
Ala Ser Gln Asn Leu Val Phe His Ser Ile Thr Arg Ser His Ala Glu
            740             745                 750
Asn Leu Gln Arg Tyr Glu Val Trp Arg Ser Asn Pro Tyr His Glu Ser
            755             760                 765
Val Glu Glu Leu Arg Asp Arg Val Lys Gly Val Ser Ala Lys Pro Phe
    770             775                 780
Ile Glu Thr Val Pro Ser Ile Asp Ala Leu His Cys Asp Ile Gly Asn
785             790             795                 800
Ala Ala Glu Phe Tyr Lys Ile Phe Gln Leu Glu Ile Gly Glu Val Tyr
            805             810                 815
Lys His Pro Asn Ala Ser Lys Glu Glu Arg Lys Arg Trp Gln Ala Thr
            820             825                 830
Leu Asp Lys His Leu Arg Lys Arg Met Asn Leu Lys Pro Ile Met Arg
            835             840                 845
Met Asn Gly Asn Phe Ala Arg Lys Leu Met Thr Gln Glu Thr Val Asp
    850             855                 860
Ala Val Cys Glu Leu Ile Pro Ser Glu Glu Arg His Glu Ala Leu Arg
865             870                 875                 880
Glu Leu Met Asp Leu Tyr Leu Lys Met Lys Pro Val Trp Arg Ser Ser
                885             890                 895
Cys Pro Ala Lys Glu Cys Pro Glu Ser Leu Cys Gln Tyr Ser Phe Asn
            900             905                 910
```

| | | | | | | | | | | | | | | | |
|---|---|---|---|---|---|---|---|---|---|---|---|---|---|---|---|
| Ser | Gln | Arg<br>915 | Phe | Ala | Glu | Leu | Leu<br>920 | Ser | Thr | Lys | Phe | Lys<br>925 | Tyr | Arg | Tyr |
| Glu | Gly<br>930 | Lys | Ile | Thr | Asn | Tyr<br>935 | Phe | His | Lys | Thr | Leu<br>940 | Ala | His | Val | Pro |
| Glu<br>945 | Ile | Ile | Glu | Arg | Asp<br>950 | Gly | Ser | Ile | Gly | Ala<br>955 | Trp | Ala | Ser | Glu | Gly<br>960 |
| Asn | Glu | Ser | Gly | Asn<br>965 | Lys | Leu | Phe | Arg | Arg<br>970 | Phe | Arg | Lys | Met | Asn<br>975 | Ala |
| Arg | Gln | Ser | Lys<br>980 | Cys | Tyr | Glu | Met | Glu<br>985 | Asp | Val | Leu | Lys | His<br>990 | His | Trp |
| Leu | Tyr | Thr<br>995 | Ser | Lys | Tyr | Leu | Gln<br>1000 | Lys | Phe | Met | Asn | Ala<br>1005 | His | Ser | Ala |
| Leu | Lys<br>1010 | Ser | Ser | Gly | Phe | Thr<br>1015 | Met | Asn | Ser | Lys | Glu<br>1020 | Thr | Leu | Gly | Asp |
| Pro<br>1025 | Leu | Gly | Ile | Glu | Asp<br>1030 | Ser | Leu | Glu | Ser | Gln<br>1035 | Asp | Ser | Met | Glu | Phe<br>1040 |

We claim:

1. A homozygous RAG-1 deficient mouse having a homozygous mutation inserted into its endogenous RAG-1 gene by homologous recombination in embryonic stem cells such that the RAG-1 gene of the mouse is non-functional or does not express a functional RAG-1 protein, and wherein the mouse has no mature B and T lymphocytes.

2. The RAG-1 deficient mouse of claim 1 wherein the mutation is an insertion, missense, frameshift, or deletion mutation.

3. The RAG-1 deficient mouse of claim 1 wherein the mutation alters a RAG-1 promoter, enhance, or splice site such that the mouse does not express a functional RAG-1 protein.

4. A method of expanding non-mouse mammalian lymphocytes in vivo in a mouse comprising:
   introducing lymphocytes from the mammal into the mouse of claim 1 thereby generating a chimeric mouse in which the lymphocytes grow.

5. The method of claim 4 further comprising depleting the animal of natural killer cells.

6. The method of claim 5 wherein the animal is depleted by treatment with anti-asialo GM1 antibodies.

7. A method of screening a compound for its effect on lymphocytes comprising:
   introducing lymphocytes from a mammal of interest into the mouse of claim 1 thereby generating a chimeric mouse;
   exposing the chimeric mouse to a compound of interest; and
   analyzing the effect of the compound on the lymphocytes.

8. A method of establishing a hematopoietic progenitor cell line comprising isolating, transforming, and culturing hematopoietic cells from the mouse of claim 1 thereby generating a hematopoietic progenitor cell line.

9. A method of determining the effect of RAG-1 on the differentiation of lymphocytes comprising transfecting the cells of the hematopoietic progenitor cell line prepared according to the method of claim 8 with a RAG-1 gene; expressing a RAG-1 gene; and determining the effect of the expression on the development of the resultant transfected cells into lymphocytes.

10. A method of determining the effect of cytokines or putative cytokines on hematopoietic progenitor cells comprising introducing into the mouse of claim 1 a cytokine or putative cytokine; isolating, transforming, and culturing hematopoietic cells from the mouse thereby generating a hematopoietic progenitor cell line, and determining the effect of the cytokine or putative cytokine on the hematopoietic progenitor cell line.

11. A method of making a mouse that develops leukemias or lymphomas by exposing the mouse of claim 1 to an agent that induces leukemia or lymphoma formation.

12. The method of claim 11 further comprising breeding the RAG-1 deficient mammal with a transgenic mammal containing activated oncogenes or tumor suppressor gene defects.

13. A method of making an immunodeficient mouse that does not contain mature B and T lymphocytes comprising:
   altering a RAG-1 coding region or a RAG-1 regulatory sequence that controls expression of the RAG-1 gene in mouse embryonic stem cells by homologous recombination thereby generating RAG-1 mutant embryonic stem cells comprising a mutant RAG-1 gene;
   introducing the RAG-1 mutant embyronic stem cells into a host mouse embryo and allowing the embryo to mature into an adult mouse; and breeding the adult mouse to yield a mouse homozygous for the mutant RAG-1 gene;
   wherein the homozygous mouse does not express a functional RAG-1 protein and has no mature B and T lymphocytes.

* * * * *